United States Patent
Viscomi et al.

(10) Patent No.: US 10,793,925 B2
(45) Date of Patent: Oct. 6, 2020

(54) LACTOBACILLUS PARACASEI FOR THE PRODUCTION OF CONJUGATED LINOLEIC ACID, NUTRITIONAL AND PHARMACEUTICAL PREPARATIONS CONTAINING IT AND USES THEREOF

(71) Applicant: ALFASIGMA S.P.A., Bologna (IT)

(72) Inventors: Giuseppe Claudio Viscomi, Bologna (IT); Annalisa Sforzini, Bologna (IT); Pierluigi Mangino, Bologna (IT); Marina Elli, Piacenza (IT)

(73) Assignee: ALFASIGMA S.P.A., Bologna (IT)

( * ) Notice: Subject to any disclaimer, the term of this patent is extended or adjusted under 35 U.S.C. 154(b) by 0 days.

(21) Appl. No.: 16/589,409

(22) Filed: Oct. 1, 2019

(65) Prior Publication Data
US 2020/0032357 A1 Jan. 30, 2020

Related U.S. Application Data

(62) Division of application No. 15/738,889, filed as application No. PCT/EP2016/065245 on Jun. 30, 2016.

(30) Foreign Application Priority Data

Jul. 7, 2015 (IT) .............................. UB2015A2376

(51) Int. Cl.
  *A61K 35/747* (2015.01)
  *A23L 33/135* (2016.01)
  *C12R 1/225* (2006.01)
  *C12N 1/20* (2006.01)
  *A61K 9/00* (2006.01)
  *A61K 9/20* (2006.01)
  *A61P 3/00* (2006.01)

(52) U.S. Cl.
  CPC ............ *C12R 1/225* (2013.01); *A23L 33/135* (2016.08); *A61K 9/009* (2013.01); *A61K 9/2095* (2013.01); *A61K 35/747* (2013.01); *A61P 3/00* (2018.01); *C12N 1/20* (2013.01); *A23V 2002/00* (2013.01)

(58) Field of Classification Search
CPC . A23L 33/135; A23V 2002/00; A61K 35/747; A61K 9/009; A61K 9/2095; A61P 3/00; C12N 1/20; C12R 1/225
See application file for complete search history.

(56) References Cited

U.S. PATENT DOCUMENTS

2009/0105341 A1 4/2009 Stanton

FOREIGN PATENT DOCUMENTS

WO 2007074010 A1 7/2007
WO 2011073769 A2 6/2011

OTHER PUBLICATIONS

Alonso L. et al., "Production of free conjugated linoleic acid by Lactobacillus acidophilus and Lactobacillus casei of human intestinal origin", J Diary Sci., (2003), vol. 86, p. 1941-1946.
Barret et al., "Rapid screening method for analyzing the conjugated linoleic acid production capabilities of bacterial cultures", Appl. Environment Microbiol., (2007), vol. 73, No. 7, p. 2333-2337.
Carafa I., et al., "Identification and characterization of wild lactobacilli and pediococci from spontaneously fermented Mountain Cheese", Food Microbiology., GB, (2015), vol. 48, pp. 123-132.
Coakley M. et al., "Conjugated linoleic acid biosynthesis by human-derived *Bifidobacterium* species", J. Appl. Microbiol., (2003), vol. 94, p. 138-145.
Ecker J. et al., "The conjugated linoleic acid isomer trans-9,trans-11 is a dietary occurring agonist of liver X receptor alpha" Biochem. Bioph. Res. Comm., (2009), vol. 388, pp. 660-666.
Ewaschuk E. et al, "Bioproduction of conjugated linoleic acid by probiotic bacteria occurs in vitro and in vivo in mice", J Nut., (2006); vol. 136(6), pp. 1483-1487.
International Search Report of PCT/EP2016/065245 dated Sep. 14, 2016.
Kramer J. et al., "Analysis of conjugated linoleic acid and trans 18:1 isomers in synthetic and animal products", Am. J. Clin., (2004), vol. 79, p. 1137-1145S.
Liu P., et al., "Production of conjugated linoleic acids by Lactobacillus plantarum strains isolated from naturally fermented Chinese pickles," Biomed. & Biotechnol., (2011), vol. 12811, pp. 923-930.
Ogawa J et al, "Production of conjugated fatty acids by lactic acid bacteria", Journal of Bioscience and Bioengineering, Elsevier, Amsterdam, NL, (2005), vol. 100, No. 4, pp. 355-364.
Ogawa J., "Conjugated linoleic acid accumulation via 10-hydroxy-12-octadecaenoic acid during microaerobic transformation of linoleic acid by Lactobacillus acidophilus", Appl. Environ. Microbiol, (2001), vol. 67, No. 3, pp. 1246-1252.

(Continued)

*Primary Examiner* — Sarvamangala Devi
(74) *Attorney, Agent, or Firm* — Silvia Salvadori, P.C.; Silvia Salvadori

(57) ABSTRACT

The present invention refers to a new strain belonging to the species *Lactobacillus paracasei* able to convert linoleic acid into conjugated linoleic acid.
The present invention refers also to nutritional or food preparations and/or pharmaceutical compositions, comprising the strain *Lactobacillus paracasei*, useful in the treatment and/or prevention of pathologies and/or physiological states related to conjugated linoleic acid deficiency or in the cases wherein the use of a probiotic is beneficial.

11 Claims, No Drawings

(56) References Cited

OTHER PUBLICATIONS

Oguz Gursoy et al., "The effect of using different probiotic cultures on conjugated linoleic acid (CLA) concentration and fatty acid composition of white pickle cheese", International Journal of Food Sciences and Nutrition, (2011) vol. 63, No. 5, pp. 610-615.

Romero-Pérez G A et al, "A rapid method of screening lactic acid bacterial strains for conjugated linoleic acid production", Bioscience Biotechnology Biochemistry, Japan Society for Bioscience, Biotechnology, and Agrochemistry, JP, (2013), vol. 77, No. 3, pp. 648-650.

Rosberg-Cody E. et al., "Mining the microbiota of the neonatal gastrointestinal tract for conjugated linoleic acid-producing bifidobacteria", Appl. Env, Microbiol, (2004), vol. 70, No. 8, p. 4635-4641.

Ryser, E.T. et al., Listeria, Listeriosis and Food Safety (3rd ed.), CRC Press, (2007), pp. 157-213.

Written Opinion of PCT/EP2016/065245 dated Sep. 14, 2016.

Campbell, et al., "Selected Fructooligosaccharide (1-Kestose, Nystose, and 1F-beta-Fructofuranosylnystose) Composition of Foods and Feeds", J. Agric. Food Chem., 1997, 45, 3076-3082.

LACTOBACILLUS PARACASEI FOR THE PRODUCTION OF CONJUGATED LINOLEIC ACID, NUTRITIONAL AND PHARMACEUTICAL PREPARATIONS CONTAINING IT AND USES THEREOF

This Non-Provisional Application is a Divisional Application of U.S. application Ser. No. 15/738,889 filed on Dec. 21, 2017, now abandoned, which is a U.S. National Stage of PCT/EP2016/0652445 filed on 30 Jun. 2016, which claims priority to and the benefit of Italian Patent Application No. UB2015A002376 filed on 7 Jul. 2015, the contents of which are incorporated herein by reference in their entireties.

STATE OF THE ART

The present invention relates to a new strain belonging to the species *Lactobacillus paracasei*, called LMG S-26420, able to convert linoleic acid (LA) into conjugated linoleic acid (CLA), useful in the treatment and prevention of diseases and/or physiological states related to conjugated linoleic acid deficiency or in cases where it is recommended the use of a probiotic, to processes for obtaining it and to pharmaceutical or nutritional compositions containing it.

The strain *Lactobacillus paracasei* LMG S-26420 is also useful in the treatment and prevention of all disorders where the assumption of a probiotic is beneficial, for example for restoring and maintaining the intestinal flora balance.

The term CLA refers to a mixture of positional and geometrical isomers of linoleic acid (LA), wherein the double bonds are conjugated in various positions, thus generating cis- and trans-isomers.

At least 16 CLA isomers are known and the isomers of major biological interest are the isomers c9-t1 and t9-t1. The isomer c9-t11 is the predominant isomer in diets, and it has proved to be important because it is involved in many biological processes and is incorporated in the phospholipidic fraction of animal tissues, which are fed with mixtures of CLA isomers.

The CLA production in human organism is substantially irrelevant and its supply is therefore entrusted to the ingestion of dairy products and meat through diet or supplements containing probiotic bacteria.

Foods produced by ruminants are the major CLA source for humans. They are intermediates in the bio-hydrogenation of linoleic acid and it is generally accepted that CIA in ruminants is originated by the incomplete bio-hydrogenation of the unsaturated acids of the linoleic acid by ruminal bacteria.

CLA is introduced in the organism through a diet with milk, fish, meat and dairy products, and its beneficial effects are correlated to daily assumption levels of about 3 g/day. An unbalanced diet gives an average CLA assumption of 0.35 g/day and, considered its beneficial effects for the organism, this deficiency must be compensated through the assumption of probiotics converting LA into CLA to provide useful dosages.

The biological activities of the conjugated linoleic acids are largely attributed to the action of isomers c9-t11 and t10-c12; the major biological activities linked to anti-carcinogenic effects are attributed to the isomer c9-t11, while the isomer t10-c12 is involved in the lipid metabolism of the human body.

CLA has important biological properties and is useful for human and animal health, such as e.g. in intestinal inflammatory pathologies, diarrhoea and colon inflammation, in increasing body mass, in increasing thermogenesis, in oxidative stress protection, in tumour prevention, in autoimmune diseases, inflammatory diseases, diabetes and atherosclerosis.

Ecker J. et al. in Biochem. Bioph. Res. Comm 388, 2009, 660-666 report that the isomer c9-t11 activates the target gene LXR involved in the development and progress of atherosclerosis. Ogawa J. et al in Appl. Env. Microbiol 2001, 67, 1246 describe the production of specific CLA isomers from linoleic acid by lactobacilli, *Lactobacillus acidophilus* in micro-aerophilic conditions, assuming that the hydroxy acid 10-hydroxy-cis-12-octadecanoid is the intermediate for this conversion and that the conversion involves more than one step.

Ogawa J. et al. in J. Bioscience Bioeng. 100 (4), 355 (2005) report the conversion of LA into CLA by bifidobacteria and lactobacilli with the obtainment of a mixture of isomers. When bifidobacteria are used, the production of CLA isomers varies from about 3 to about 400 mg per litre of culture, while when lactobacilli are used, the productivity varies from about 100 mg to about 4 g per litre of culture. When *Lactobacillus casei* are used, the productivity never exceeds 1 g per litre of culture.

Rosberg-Cody E. et al in Appl. Env. Microbiol 70 (8) 4635, 2004 describe the isolation of bifidobacteria strains from new-born faecal material, useful for the production of CLA, and suggest the use of those bacteria in supplements for new-borns at risk of necrotizing enterocolitis.

Also Coakley M. et at in J. Appl. Microbiol. 94, 138 (2003) describe the ability of *Lactobacillus, Lactococcus* and *Bifidobacteria* to convert LA into CLA, and demonstrate that bifidobacteria strains have a higher ability of conversion of LA into CLA, with conversion percentages up to almost 65%.

Alonso L. et al. in J Diary Sci. 86, 1941 (2003) describe the conversion of LA into CLA by *Lactobacilli casei* and *Lactobacilli acidophilus* of human intestinal origin in media added with different concentrations of linoleic acid. At concentrations of 0.02% of linoleic acid, the maximum CLA concentration obtained with *Lactobacillus casei* is about 110 mg per litre of culture and the amount of the isomer of biological interest c9-t11 ranges from 60 to 85 mg per litre of culture.

Gustavo A. et al, in Biosci. Biotechnol. Biochem., 77 (3), 648-650, 2013, describe a rapid and simpler method to screen conjugated linoleic acid (CLA)-producing bacteria isolated from cow milk. One strain resembling a *L. paracasei* converted free linoleic acid to total CLA in a percentage greater than 85%. However the percentage of conversion in CLA isomer of biological interest c9, t11 is only about 18%.

Oguz Gursoy et al, in International Journal of Food Sciences and Nutrition, 63(5), 610-615, describe the effect of using different probiotics cultures on conjugated linoleic acid concentration and fatty acid composition of cheese. They report that the probiotic differences and storage process have not affected the CLA contents of the samples statistically. The increment of CLA content of cheese samples is due to lipolysis of the free linoleic acid by lactic acid bacteria.

The assumption of probiotic products comprising lactobacilli is also useful for maintaining the intestinal bacterial flora balance and is a useful tool in the prevention and treatment of dysbiosis in general, where the balance between bifidobacteria and lactobacilli is essential.

Given the low amount of CLA introduced with the diet, and the dosage useful in all pathologies and disorders connected to a CIA deficiency, there was the need to have available bacteria converting LA into CLA for obtaining daily dosages useful for the health of individuals and for the treatment of all pathologies where CLA isomers are beneficial.

Bifidobacteria convert LA into CLA, but bifidobacteria cultures have the disadvantage of having low productivity yields, meant as number of bacteria per litre of culture, and therefore it is not easy to obtain them in large amounts in industrial scale processes.

Therefore, there was the need to have a bacterial strain able to convert LA into CLA obtainable by bacterial cultures with high productivity to be used in pharmaceutical or nutritional preparations useful in the treatment or prevention of all disorders and pathologies related to a CLA deficiency.

There was also the need to have a bacterial strain belonging to the genera *Lactobacillus*, able to convert LA into CLA isomers beneficial for humans or animals. Moreover, there was also the need to have a lactobacillus for all disorders or pathologies associated with a microbial imbalance on the body surface. A strain belonging to the lactic genus can be ingested in association with bacteria of the genus *Bifidus* to promote the microbial balance of human or animal flora.

The bacteria belonging to the genus *Lactobacillus* are among those with the highest productivity; therefore, they are preferable to those belonging to the genus *Bifidobacterium* to convert LA into CLA. *Lactobacilli* can be obtained by industrial processes with higher yields than bifidobacteria, and can be used for the production of nutritional or pharmaceutical compositions for the administration in human or animal.

Among these, lactobacilli able to convert LA into isomers c9-t11 and t9-t11 of CLA to a greater extent than the other isomers are preferred. c9-t11 is a major isomer because it is involved in cell membrane phospholipids and is the predominant isomer in diets. These isomers have beneficial effects on humans and animals, and in particular the isomer t9-t11 has anti-proliferative and anticancer properties. Ecker J et al. in Biochem. Biophysical. Res. Comm 388, 660, 2009 report that the isomer t9-t11 of CLA is a powerful agonist of macrophagic LXR, linked to the inflammation induction processes, and it has an important role in the reduction of arteriosclerotic processes in animal models.

The present invention describes a strain belonging to the genus *Lactobacillus*, named *Lactobacillus paracasei* LMG S-26420, able to convert LA into CLA with a conversion percentage higher than the other lactobacilli strains known in the art. Moreover, the strain LMG S-26420 of the present invention is characterized by converting LA into CLA, wherein the mixture of isomers c9-t11 and t10-c12 is prevalent if compared to the other isomers.

The strain is obtained with bacterial cultures characterized by a productivity higher than 4 g per litre of culture and it can be obtained in lyophilic form.

The strain is stable and the product of the bacterial culture can be stored for long periods at temperatures lower than 0° C. or for periods longer than 6 months at 4° C. in lyophilic form. The strain LMG S-26420 can be comprised in nutritional or food preparations or in pharmaceutical compositions useful for the treatment and/or the prevention of disorders or pathologies linked to a CLA deficiency and in all disorders wherein a probiotic assumption is beneficial for humans or animals.

SUMMARY

The present invention describes a new strain belonging to the genus *Lactobacillus*, named *Lactobacillus paracasei*, filed at the Belgian Coordinated Collections of Microorganisms BCCM/LMG Bacteria Collection—Microbiology Laboratory—Gent University on Apr. 15, 2011 with the number LMG S-26420.

The *Lactobacillus paracasei* LMG S-26420, is characterized in that it converts linoleic acid in conjugated linoleic acid in a percentage higher than 30%.

The strain *Lactobacillus paracasei* LMG S-26420 is characterized by converting linoleic acid (LA) into conjugated linoleic acid (CLA), in a percentage higher than 30% if compared to the starting LA, wherein the biological isomers with biological activity c9-t11 and t9-t11 are in a percentage higher than 30% if compared to the other CLA isomers.

The strain *Lactobacillus paracasei* LMG S-26420 is characterized by the production of high concentration of CLA.

The strain *Lactobacillus paracasei* LMG S-26420 is obtained by bacterial cultures characterized by a productivity higher than 4 g per litre of culture and a yield of Colony Forming Units (CFU) higher than $1 \times 10^9$ per millilitre of culture.

The strain *Lactobacillus paracasei* LMG S-26420 is characterized by being stable: it can be stored at temperatures lower than 0° C. and for periods longer than 6 months at 4° C. in lyophilic form.

The strain lyophilic *Lactobacillus paracasei* LMG S-26420 is characterized by an amount of living cells higher than $1 \times 10^{10}$, in particular from about $1 \times 10^{10}$ to about $7 \times 10^{10}$ unit per grain of lyophilic product.

It is an object of the present invention the process for the production of the strain *Lactobacillus paracasei* LMG S-26420 in bacterial culture, wherein the inoculum of the strain LMG S-26420 has a concentration from 0.1 to 10% (v/v) in a culture medium at a temperature comprised between 30° C. and 37° C., at pH values comprised between 4.5 and 7.5, for a period comprised between 6 and 15 hours. The biomass is separated and it can be preserved at temperatures lower than 4° C. or submitted to lyophilisation processes.

The described process leads to the obtainment of the strain *Lactobacillus paracasei* LMG S-26420 with a number of colony-forming units comprised between $1 \times 10^9$ and $5 \times 10^9$ CFU per millilitre of culture and with a biomass in an amount comprised between 10 and 20 grams per litre of culture.

The process comprising the lyophilisation leads to the obtainment of the strain LMG S-26420 in solid form. In the presence of cryoprotectants, the strain is obtained with yields of colony-forming units (CFU) higher than 50% and the lyophilic strain LMG S-26420 includes an amount of cells higher than $1 \times 10^{10}$ per gram of lyophilic product.

Objects of the invention are nutritional or food preparations and pharmaceutical compositions comprising an amount of *Lactobacillus paracasei* LMG S-26420 in lyophilic form corresponding to an amount of living cells from about $1 \times 10^8$ to about $5 \times 10^{11}$.

Nutritional or food preparations and pharmaceutical compositions comprising *Lactobacillus paracasei* LMG S-26420 can be in form of sachets, tablets or capsules. The nutritional or food preparations and the pharmaceutical compositions can comprise prebiotics, vitamins, mineral salts and pharmaceutical or nutritional excipients.

The prebiotics are comprised in *Lactobacillus paracasei* LMG S-26420 compositions, selected from the group consisting of fructo-oligosaccharides, inulines, galacto-oligosaccharides, xilo-oligosaccharides, isomalto-oligosaccharides and vitamins selected from the group comprising the vitamins of the E and B complex.

The nutritional or food preparations and pharmaceutical compositions comprising *Lactobacillus paracasei* LMG S-26420 can comprise bifidobacteria.

The compositions comprising *Lactobacillus paracasei* LMG S-26420 are useful in the treatment and prevention of pathologies and/or physiological states related to the deficiency of conjugated linoleic acid and in all other cases wherein the use of a probiotic is useful and has a beneficial effect.

In particular, the compositions comprising *Lactobacillus paracasei* LMG S-26420 are useful in the treatment and prevention of pathologies and/or physiological states related to a CLA deficiency, such as e.g. in intestinal inflammatory pathologies, as dianhoeal and colon inflammation; in increasing body mass, in increasing thermogenesis, in oxidative stress protection, in tumour prevention, in autoimmune diseases, diabetes and atherosclerosis.

The compositions comprising *Lactobacillus paracasei* LMG S-26420 with bifidobacteria, object of the present invention, are useful in the treatment of all disorders related to bacterial dysbiosis.

The compositions comprising *Lactobacillus paracasei* LMG S-26420 are useful in all physiological states where the intestinal bacterial flora balance of humans and animals must be kept unaltered.

DESCRIPTION OF THE INVENTION

A pure bacterial culture of the strain belonging to the *Lactobacillus paracasei* was filed at the Belgian Coordinated Collections of Microorganisms—BCCM/LMG Bacteria Collection—Microbiology Laboratory—Gent University with the number LMG S-26420.

The present invention refers to a new strain of *Lactobacillus paracasei* LMG S-26420, to pharmaceutical, nutritional or food compositions comprising said strain and to their use in the treatment and prevention of pathologies and/or physiological states related to the deficiency of conjugated linoleic acid or when the use of a probiotic is suggested.

The strain *Lactobacillus paracasei* LMG S-26420 has been isolated from the vaginal bacterial flora of a healthy woman, selected among many other strains of lactobacilli simultaneously isolated from the same source and from other types of biological samples and among other strains of the same species, because it has shown an ability to convert linoleic acid (LA) into conjugated linoleic acid (CLA). This characteristic makes this strain a probiotic agent useful for human and animal use.

*Lactobacillus paracasei* LMG S-26420 is characterized by converting LA into CLA in a percentage higher than 30% determined by chromatographic method.

*Lactobacillus paracasei* LMG S-26420 converts LA into isomers of CLA with biological activity, in particular in the isomers c9-t11 and t9-t11. In a particular aspect of the invention, *Lactobacillus paracasei* LMG S-26420 converts LA into the isomers c9-t11 and t9-t11 of CLA in a percentage higher than 30%.

To evaluate the ability of the strain *Lactobacillus paracasei* LMG S-26420 to convert LA into CLA, three different methods were used: the Ogawa method, the Liu method and the chromatographic method.

The use of the Ogawa J. method described in Appl. Environ. Microbiol 67(3): 1246-1252, 2001 allows determining the ability of the strain *Lactobacillus paracasei* LMG S-26420 to convert LA into CLA in a suitable culture medium by adding LA to the bacterial culture in order to metabolically adapt the cells.

In a first case, variable concentrations of LA, in a range from 0.01 mg/ml to 1 mg/ml, are added to a series of cell cultures of the strain LMG S-26420 and cells are incubated for a period from 1 to 4 days at temperatures from 30° to 40° C. The final product is centrifuged and a constant concentration of LA, equal to 5 mg/ml, was added to the cells. The cell cultures are incubated at a temperature ranging from 30° to 40° C., for a period from 40 to 80 hours and then centrifuged to remove the supernatant. To evaluate the ability of a strain to convert LA into CLA, the cells are resuspended in water and CLA is determined by spectrophotometric method.

In a second case, a constant concentration of LA equal to 5 mg/ml is added to a series of cell cultures of *Lactobacillus paracasei* LMG S-26420 and the biomass obtained at the end of the culture is incubated with variable concentrations of LA in a range from 0.05 mg/ml to 0.4 mg/ml.

In both cases, *Lactobacillus paracasei* LMG S-26420 shown to be effective in converting LA into CLA, in particular in a percentage higher than 30%.

The use of the Liu P. method as described in Biomed. & Biotechnol. 12811, 923-930, 2011, comprises the inoculation of the strain LMG S-26420 in an adequate culture medium with LA concentrations from 0.05 to 1 mg/ml. The cultures are incubated for a period from 1 to 3 days at temperatures from 30° C. to 40° C. and then centrifuged. The CLA concentrations is determined by means of spectrophotometric method.

The trials carried out according to the Ogawa and Liu methods showed the ability of the strain *Lactobacillus paracasei* LMG S-26420 to convert LA into CLA. However, it is not possible to evaluate the percentage of conversion into CLA isomers with these methods, in particular if the strain is able to convert LA into CLA isomers having the strongest biological activity.

The chromatographic method, in turn, allows the separation and quantification of CLA geometrical isomers, isomers trans-trans, trans-cis and cis-cis, in particular isomers cis9-trans 11, trans 10-cis 12 and trans 9-trans 11.

The obtained CLA isomers were determined by using silver-ion high-pressure liquid chromatography (HPLC) with a diode array detector and a UV detector at 234 nm.

The chromatographic method demonstrates that the strain LMG S-26420 converts LA into CLA with a percentage higher than 30%.

The chromatographic method demonstrates that the strain LMG S-26420 converts LA into CLA with a percentage from 30% to 50%, wherein the percentage of isomers with biological activity, c9-t11 and t9-t11, are prevalent if compared to the other isomers. In particular, the strain LMG S-26420 converts LA into CLA isomers c9-t11 and t9-t11, wherein their percentage is 40% higher than all other CLA geometrical isomers.

The strain LMG S-26420 is obtained by cell cultures characterized by giving a number of colony forming units (CFU) higher than $1 \times 10^9$ per millilitre and an amount of solid mass higher than 4 g per litre of culture. The obtained new bacterial strain is stable at temperatures lower than 4° C. for longer periods and it can be lyophilised with processes that significantly preserve cell viability. The lyophilic products are stable for periods of time longer than 3 months at temperatures of 4° C. and 25° C.

The strain *Lactobacillus paracasei* LMG S-26420 produces an amount of lyophilised biomass higher than 4 g per litre of culture, in particular from 10 to 20 g per litre of culture. Considering the ability of this strain to convert LA into CLA in a percentage higher than 30%, it can be stated that the new strain *Lactobacillus paracasei* LMG S-26420 is able to produce remarkable concentrations of CLA. For example, adding *Lactobacillus paracasei* LMG S-26420 to solutions including concentrations of about 500 mg/litre of linoleic acid leads to obtain concentrations higher than 250 mg/litre of conjugated linoleic acid.

Another advantage of the present invention is to have a new strain belonging to the genus *Lactobacillus* for the conversion of LA into CLA isomers with high conversion yields useful to be included in nutritional or food preparations or in pharmaceutical compositions.

The new strain *Lactobacillus paracasei* LMG S-26420 can be comprised in compositions also comprising other bacterial strains, belonging to the same genus or not, like bifidobacteria.

The compositions comprising LMG S-26420 and other bacterial strains advantageously generate a heterogeneous probiotic population, useful to maintain the intestinal bacterial flora balance.

The bacterial cultures object of the present invention were produced first in laboratory scale and then in industrial scale. The bacterial culture of LMG S-26420 was obtained by means of a fermentation process in a period from 6 to 12 hours at temperatures ranging from 30° C. to 40° C. in a medium named MRS® (De Man, Rogosa & Sharpe) containing as main ingredients yeast extract, mixtures of peptones and glucose in addition to potassium salts, ammonium, magnesium and manganese.

Starting from the primary cultures, many expansion phases were conducted to increase the number of cells per volume of culture of the pure strain in order to obtain the so called "mother cultures", that were used as inoculum for the industrial production of the bacterial cultures of the probiotic LMG S-26420.

The industrial process for the production of *Lactobacillus paracasei* LMG S-26420 comprises the following steps:

inoculating the strain LMG S-26420 with volumes of mother cultures, in a volumetric percentage from 0.1 to 10% and fermenting in an adequate medium of culture at 37° C. and pH from 4.5 to 7.5, for a period from 8 to 15 hours;

separating the bacterial biomass from the culture broth by centrifugation.

The biomass can be frozen or submitted to lyophilisation processes after adding suitable cryoprotectants, selected among soluble carbohydrates, which are useful to maintain the cell viability during the lyophilisation processes.

The strain LMG S-26420 is obtained by fermentation processes characterized by producing a number of living cells higher than $10^9$ living cells per ml of culture and a lactobacilli biomass higher than 4 g per litre of culture.

The strain LMG S-26420 is obtained with a productivity from $1\times10^9$ to $7\times10^9$ living cells per ml of culture and has a yield of dried product from 10 to 20 g per litre.

The cell viability is determined using bacterial counting methods known to the person skilled in the art.

The strain LMG S-26420 obtained from the described cultures can be lyophilised to be easily stored and to be included in alimentary, food or pharmaceutical preparations.

The lyophilisation process was executed in the presence of cryoprotectants chosen among soluble carbohydrates, such as for example trealose and cyclodextrins or a mixture of them. The described lyophilisation process is characterized by obtaining a lyophilic strain LMG S-26420 with a yield in vital cells higher than 50% than before the lyophilisation process. The strain LMG S-26420 is characterized by comprising an amount of living cells per gram of lyophilic product higher than almost $1\times10^{10}$, in particular from almost $1\times10^{10}$ to almost $7\times10^{10}$ per gram of lyophilic product. This confirms that the strain *Lactobacillus paracasei* LMG S-26420 is characterized by a high productivity, can be lyophilised and maintained as lyophilic product with the certainty of preserving cell viability.

The strain *Lactobacillus paracasei* LMG S-26420 obtained with the described cell cultures and lyophilised in presence of cryoprotectants selected among soluble carbohydrates or mixtures thereof, is characterized by a water activity ($a_w$) lower than 0.6, a value below which the proliferation of the majority of bacteria and mildews is inhibited. The water activity is a value obtained by measuring the partial steam pressure in a substance divided by the partial pressure of water, and is obtainable with detectors directly giving those values.

As described by Ryser, E. T. et al in *Listeria*, Listeriosis and Food Safety (3rd ed.). CRC Press. 173-174, (2007), water activity values lower than 0.6 assure that the lyophilic preparation can be stored because it does not degrade because of microbial proliferation, which is one of the most dangerous causes of alimentary or food alterations.

The lyophilic products of the strain LMG S-26420s are characterized by having an elevated number of living cells per gram of lyophilic product and a low content of water activity, are useful to be stored for the preparation of compositions or preparations in different forms containing different probiotic amounts, with no limitation.

The LMG S-26420 bacterial strain in the solutions submitted to the lyophilisation processes is characterized by values of glass transition temperatures, $T_g$, higher than 100° C., and in the presence of soluble carbohydrates, such as e.g. trealose, the values of glass transition temperatures are in a range from 100° C. to 120° C. These values confirm that this strain can be submitted to lyophilisation and vacuum drying processes up to temperatures of 100° C. without having the product converted into a glassy state, with a consequent loss of its properties.

The glass transition temperature of frozen solutions $T_g'$ relating to the preparations to be lyophilised is in a range from $-15°$ to $-30°$ C. and in the presence of soluble carbohydrates, as e.g. trealose, the glass transition temperatures are in a range from $-20$ to $-30°$ C.

The lyophilisation process of the strain *Lactobacillus paracasei* LMG S-26420 described in Example 3 in the presence of cryoprotectants chosen among soluble carbohydrates, in particular trealose, is characterized by a freezing step carried out at temperatures lower than $-30°$ C. and a secondary drying carried out at temperatures lower than 100° C. Said process leads to the obtainment of the strain LMG S-26420 in lyophilic form, which is characterized by maintaining its biological properties.

In particular, the lyophilisation process of the strain *Lactobacillus paracasei* LMG S-26420 described in the invention in the presence of trealose maintains a cell viability higher than 30%, in particular 30% to 60%, if compared to the cell viability before lyophilisation.

The described lyophilic compositions of the strain *Lactobacillus paracasei* LMG S-26420 comprise soluble carbohydrates, such as trealose and mannitol; this latter can be added to trealose-comprising lyophilic preparations when a high lyophilic mass is requested, in particular to be used in preparations with a low dosage of probiotic strain.

The solutions comprising *Lactobacillus paracasei* LMG S-26420 to be lyophilised can comprise osmolytes chosen from the group consisting of betaine, sarcosine, glycerol, erythritol; salts selected from the group consisting of acetates, formiates or ammonium salts, useful to maintain pH values between 4 and 8 during the lyophilisation process.

The lyophilic strain *Lactobacillus paracasei* LMG S-26420 is stable at a temperature of 4° C. for a period longer than 3 months. In a particular aspect, *Lactobacillus paracasei* LMG S-26420 maintains more than 70% of its cell viability after 6 months at the temperature of 4° C., and the water activity remains with values lower than 0.6%.

The lyophilic product can therefore be prepared in large amounts and be stored for the preparation of compositions in solid or suspended form at different probiotic dosages.

An aspect of the present invention refers to pharmaceutical compositions, nutritional or food preparations comprising variable amounts of the strain LMG S-26420 in lyophilic form in amounts ranging from 20 to 2500 mg. These compositions are characterized by comprising an amount of living cells of LMG S-26420 from $1 \times 10^9$ to $1 \times 10^{11}$ per gram of lyophilic product.

The preparations can be in a form useful for oral administration, such as e.g. in sachets, tablets, capsules or liquid suspensions.

The compositions in form of tablets or capsules can comprise an amount of the strain *Lactobacillus paracasei* LMG S-26420 ranging from 20 to 800 mg and the sachet compositions for liquid suspension can comprise an amount of *Lactobacillus paracasei* LMG S-26420 ranging from 20 mg to 10 grams. The pharmaceutical or nutritional compositions can comprise an amount of *Lactobacillus paracasei* LMG S-26420 ranging from about $1 \times 10^9$ to $1 \times 10^{11}$ unity of cells.

The pharmaceutical, nutritional or food compositions comprising *Lactobacillus paracasei* LMG S-26420 can optionally comprise, but are not limited to, prebiotics selected from the group consisting of fructo-oligosaccharides, inulines, galacto-oligosaccharides, xilo-oligosaccharides, isomalto-oligosaccharides, resistant dextrin, polydextrose, arabino-galactans, resistant starch, dextrans, guar gum; amino acids; proteins; antioxidants; vitamins selected from the group comprising the vitamins of the E and B complex, together with pharmaceutically acceptable salts useful for the preparation of the desired form.

The pharmaceutical, nutritional or food compositions comprising *Lactobacillus paracasei* LMG S-26420 can comprise also other bacteria able to convert LA into CLA, in particular those belonging to the genus *Bifidobacterium*. These compositions increase the conversion of LA into CLA and favour the intestinal bacterial flora balance.

The compositions in form of sachets are prepared by mixing the strain *Lactobacillus paracasei* LMG S-26420 in form of lyophilic products with selected excipients, such as e.g. oligosaccharides, selected from the group of fructo-oligosaccharides, inulines, galacto-oligosaccharides, xilo-oligosaccharides, isomalto-oligosaccharides and flavours, previously sieved. The homogeneous mixture is then divided in sachets.

The lyophilic form can be grinded or granulated before being added to the pharmaceutical excipients chosen for the preparation of the desired solid forms.

The compositions in form of tablets can comprise diluents, ligands, disintegrants, lubricants, glidants and are prepared according to the techniques known to the person skilled in the art.

Optionally, the compositions can comprise preservatives, antioxidants, buffering, colouring, flavouring and sweeting agents.

The compositions of the invention comprising the strain *Lactobacillus paracasei* LMG S-26420 are stable at temperature of 4° C. and 25° C. for a period of 1, 3 and 6 months with a complete recovery of the living cells.

Another aspect of the invention refers to the use of pharmaceutical, nutritional or food compositions comprising the strain *Lactobacillus paracasei* LMG S-26420 for use in the treatment and prevention of pathologies and/or physiological states wherein a probiotic is useful. These compositions are useful in the prevention and treatment of pathologies and/or physiological states related to a CLA deficiency such as, e.g. in intestinal inflammatory pathologies, diarrhoea and colon inflammation, in increasing body mass, in increasing thermogenesis, in oxidative stress protection, in tumour prevention, autoimmune diseases, inflammatory diseases, diabetes and atherosclerosis.

The compositions comprising the strain *Lactobacillus paracasei* LMG S-26420 are useful in the treatment and prevention of all disorders or pathologies connected to a microbial unbalance.

The compositions comprising the strain *Lactobacillus paracasei* LMG S-26420 are also useful as alimentary supplement in all diets poor of meat or milk products to obtain CLA concentrations beneficial for humans.

EXAMPLES

The Examples refer to the strain *Lactobacillus paracasei* LMG S-26420 exactly corresponding to the one filed at the Belgian Coordinated Collection of Microorganisms, BCCM, LMG Bacteria Collection, Microbiology Laboratory, Gent University, which confirmed the purity and viability of the strain and registered it with the number LMG S-26420.

Example 1

Determination of the Strain Ability to Convert Linoleic Acid (LA) Into Conjugated Linoleic Acid (CLA)

To determine the ability of the strain *Lactobacillus paracasei* LMG S-26420 to convert LA into CLA, it has been evaluated a condition wherein the inoculum was made in presence of LA, to stimulate bacterial cells pre-adaptation, and a condition without LA.

a) Determination According to the Ogawa Method

The quantitative determination of the ability of *Lactobacillus paracasei* LMG S-26420 to convert LA into CLA was carried out according to the Ogawa method described in Appl. Envr. Microbiol. 2001, 67, 1246.

The method is based on the inoculum of the strain in MRS® (Man, Rogosa, Sharpe) cultural medium comprising a mixture of peptones 18 g/l; yeast extract 4 g/l; glucose 20 g/l; TWEEN-80® 1 ml/l; potassium phosphate 2 g/l; tri-ammonium citrate 2 g/l; anhydrous sodium acetate 3 g/l; heptahydrate magnesium sulphate 0.2 g/l; anhydrous magnesium sulphate 0.034 g/l; agar 12 g/l.

The strain *Lactobacillus paracasei* LMG S-26420 at a concentration of 1% was inoculated in 15 ml of MRS® with LA at concentrations from 0.01 to 0.4 mg/ml and the solutions were kept at a temperature of 37° C. for 3 days at low stirring. The cultures were centrifuged and the supernatant was eliminated. The pellet was washed with sterile water and the cell mass of about 20 mg was resuspended with 1 ml of solution of potassium phosphate buffer 100 mM at pH 6.5 and 5 mg of LA in a complex with bovine albumin (BSA) were added to cell suspension, with a ratio corresponding to 0.2 mg BSA/mg of LA. The cultures were then incubated for 48 and 72 hours and then centrifuged to eliminate the supernatant. The cells were resuspended in water and the CLA concentration was spectrophotometrically determined by means of the Barret method, described in Appl. Environment Microbiol. 73(7), 2333, (2007). This method comprises the extraction of the fatty acid fraction by the addition of 2 ml of isopropanol to 1 ml of sample. The solutions were vigorously stirred, allowed to stand for 3 minutes and then 1.5 ml of hexane were added. Organic phases were separated and dehydrated with anhydrous sodium sulphate and the CLA amount was determined by spectrophotometric reading at 233 nm. The concentrations were determined by a calibration curve obtained with different concentrations of the CLA isomer c9-t11 at the same wavelength.

Table 1 reports the conversion percentages of LA into CLA by means of the strain *Lactobacillus paracasei* LMG S-26420, wherein the pre-incubation of the strain was carried out at different concentrations of LA and the incubation of the washed cells was carried out with 5 mg/ml of LA. Table 1 shows that, in the reported conditions, the conversion percentages of LA into CLA range from 1% to 7%.

TABLE 1

| LA concentration (mg/ml) | Cell incubation time (h) | Cell incubation temperature (° C.) | CLA concentration (mg/ml) | Conversion percentage (%) of LA into CLA |
|---|---|---|---|---|
| 0.01 | 48 | 30 | 0.083 | 2 |
| 0.05 | 48 | 30 | 0.075 | 2 |
| 0.1 | 48 | 30 | 0.067 | 1 |
| 0.2 | 48 | 30 | 0.041 | 1 |
| 0.3 | 48 | 30 | 0.045 | 1 |
| 0.4 | 48 | 30 | 0.104 | 2 |
| 0.01 | 72 | 37 | 0.204 | 4 |
| 0.05 | 72 | 37 | 0.273 | 5 |
| 0.1 | 72 | 37 | 0.097 | 2 |
| 0.2 | 72 | 37 | 0.349 | 7 |
| 0.3 | 72 | 37 | 0.282 | 6 |
| 0.4 | 72 | 37 | 0.085 | 6 |

Under the conditions reported in Table 2, CLA is not present in the supernatant.

Table 2 reports the results of the conversion of LA into CLA. The pre-incubation was carried out with LA at a concentration of 0.05 mg/ml and the washed cell mass was incubated at a variable concentration of LA. CLA was determined on the supernatant and on the cell pellet.

TABLE 2

| LA concentration (mg/ml) | Cell incubation time (h) | Cell incubation temperature (° C.) | Sample | CLA concentration (mg/ml) | Conversion percentage (%) of LA into CLA |
|---|---|---|---|---|---|
| 0.05 | 72 | 37 | Cells | — | — |
| 0.05 | 72 | 37 | Supernat. | 0.013 | 25 |
| 0.1 | 72 | 37 | Cells | — | — |
| 0.1 | 72 | 37 | Supernat. | 0.004 | 4 |
| 0.2 | 72 | 37 | Cells | — | — |
| 0.2 | 72 | 37 | Supernat. | — | — |
| 0.3 | 72 | 37 | Cells | — | — |
| 0.3 | 72 | 37 | Supernat. | — | — |
| 0.4 | 72 | 37 | Cells | 0.007 | 2 |
| 0.4 | 72 | 37 | Supernat. | 0.005 | 1 |
| 0.5 | 72 | 37 | Cells | 0.007 | 1 |
| 0.5 | 72 | 37 | Supernat. | 0.003 | 1 |
| 1 | 72 | 37 | Cells | 0.025 | 3 |
| 1 | 72 | 37 | Supernat. | — | — |
| 2 | 72 | 37 | Cells | 0.042 | 2 |
| 2 | 72 | 37 | Supernat. | 0.011 | 1 |
| 3 | 72 | 37 | Cells | 0.059 | 2 |
| 3 | 72 | 37 | Supernat. | 0.017 | 1 |
| 4 | 72 | 37 | Cells | 0.077 | 2 |
| 4 | 72 | 37 | Supernat. | 0.0043 | 1 | b) Determination According to the Liu Method

The Liu method has been described in Biomed. Biotechnol. 12811, 923 (2011).

Table 3 reports data related to the conversion of LA into CLA by *Lactobacillus paracasei* LMG S-26420, according to the method described by Liu P et al. in Biomed. Biotechnol. 12811, 923, 2011.

The method is based on the determination of the CLA amount in the supernatant of cultures in MRS® medium containing different concentrations of LA from 0.05 to 0.5 mg/ml. The cultures were incubated for a period of 24 and 96 hours and at temperature of 30° and 37° C. The CLA obtained by the conversion of LA was determined with the Barret method as described in the Example 1.a.

TABLE 3

| LA concentration (mg/ml) | Cell incubation time (hours) | Cell incubation temperature (° C.) | CLA concentration (mg/ml) | Conversion percentage (%) of LA into CLA |
|---|---|---|---|---|
| 0.00 | 24 | 30 | 0.001 | — |
| 0.05 | 24 | 30 | 0.005 | 9 |
| 0.1 | 24 | 30 | 0.005 | 5 |
| 0.2 | 24 | 30 | 0.005 | 2 |
| 0.3 | 24 | 30 | 0.006 | 2 |
| 0.4 | 24 | 30 | 0.006 | 2 |
| 0.5 | 24 | 30 | 0.006 | 1 |
| 0.00 | 96 | 30 | 0.001 | — |
| 0.05 | 96 | 30 | 0.006 | 12 |
| 0.1 | 96 | 30 | 0.005 | 5 |
| 0.2 | 96 | 30 | 0.005 | 3 |
| 0.3 | 96 | 30 | 0.006 | 2 |
| 0.4 | 96 | 30 | 0.006 | 1 |
| 0.5 | 96 | 30 | 0.006 | 1 |
| 0.00 | 24 | 37 | 0.001 | — |
| 0.05 | 24 | 37 | 0.004 | 8 |
| 0.1 | 24 | 37 | 0.005 | 5 |
| 0.2 | 24 | 37 | 0.005 | 2 |
| 0.3 | 24 | 37 | 0.005 | 2 |
| 0.4 | 24 | 37 | 0.006 | 1 |
| 0.5 | 24 | 37 | 0.006 | 1 |
| 0.00 | 96 | 37 | 0.001 | — |
| 0.05 | 96 | 37 | 0.005 | 10 |
| 0.1 | 96 | 37 | 0.006 | 6 |
| 0.2 | 96 | 37 | 0.006 | 3 |
| 0.3 | 96 | 37 | 0.007 | 2 |
| 0.4 | 96 | 37 | 0.006 | 2 |
| 0.5 | 96 | 37 | 0.008 | 2 | c) Determination According to the Chromatographic Method (HPLC)

The chromatographic method allows the determination of CLA geometrical isomers, the isomer c9-t11, the isomer trans 10-cis12 and the isomer trans9-trans11 in cell suspensions and in supernatants of cultures according to the method described in a) and in b) and reported in Tables 2 and 3.

The samples were methylated as described by Kramer J. et al. in Am. J. Clin. 79, 1137 S 2004 and the obtained methyl esters were separated by silver-ion high-pressure chromatography (HPLC). CLA isomers were separated using three 4.6 mm×250 mm CHromSpher Lipid columns, connected in series, with 5μ-sized particles. The isomers were eluted with a solution of hexane-acetonitrile: 99-1 and detected with a diode array detector and a UV detector at 234 nm in series. The quantitative determination was carried out by using solutions at known concentrations of CLA isomers.

Table 4a reports the determination of CLA isomers in pellet samples coming from cultures with LA pre-incubation at a concentration of 0.05 mg/ml and incubation of washed cells at different concentrations of LA at 37° C. and an incubation time of 72 hours as reported in a), Ogawa method.

TABLE 4A

| LA conc. (mg/ml) | CLA isomer t9-t11 (mcg/g) | CLA isomer c10-t12 (mcg/g) | CLA isomer c9-t11 (mcg/g) | Isomers (t9-t11 and c9-t11)* (%) | Total conversion percentage (%) |
|---|---|---|---|---|---|
| 0.05 | 1.39 | 2.75 | 2.07 | 3.46 | 14.8 |
| 0.01 | 1.56 | 3.50 | 3.07 | 4.63 | 0.2 |
| 0.4 | 1.21 | 2.78 | 2.40 | 3.61 | 0.2 |

*isomers with biological activity

Table 4b reports the concentration of CLA isomers in supernatant samples coming from cultures incubated at different concentrations of LA as reported in b), Liu method.

TABLE 4b

| LA conc. (mg/ml) | CLA isomer t9-t11 (mcg/g) | CLA isomer c10-t12 (mcg/g) | CLA isomer c9-t11 (mcg/g) | CLA isomer (t9-t11 and c9-t11)* (mcg/g) | Isomers (t9-t11 and c9-t11)* (%) | Total conversion percentage (%) |
|---|---|---|---|---|---|---|
| 0.05 (24 h) | 1.81 | 5.07 | 3.30 | 44.16 | 46.76 | 25.9 |
| 0.05 (96 h) | 2.45 | 6.33 | 5.06 | 42.26 | 46.67 | 35.5 |
| 0.2 (96 h) | 1.74 | 5.64 | 5.04 | 46.15 | 46.15 | 7.3 |
| 0.5 (96 h) | 1.95 | 5.80 | 5.22 | 7.17 | 44.67 | 3.2 |

*isomers with biological activity

Example 2

Fermentation Process for the Preparation of the Strain *Lactobacillus paracasei* LMG S-26420.

The fermentations were carried out in a Sartorius fermenter. The inoculum of the strain *Lactobacillus paracasei* LMG S-26420 at 1%, corresponding to 40 ml, was cultured in 4 litres of MRS® medium at a temperature of 37° C. for 8 hours.

The cell mass obtained by different fermentations was concentrated by centrifugation and washed with sterile water. The optic density on the aqueous suspension of the cell mass was determined by spectrophotometric method at 625 nm and the Colony Forming Units (CFU) were determined by decimal plate count.

Some preparations were carried out with different fermentation parameters in order to determine the best bacterial growing conditions for the strain *Lactobacillus paracasei* LMG S-26420.

Table 5 reports the parameters related to fermentations at different carbon dioxide pressures, stirring speed and pH. Table 5 also reports the results obtained by measuring the optic density and the CFU number on biomass at fermentation end, after 8 hours.

TABLE 5

| Fermentation parameters | Prep. 1 | Prep. 2 | Prep. 3 | Prep. 4 | Prep. 5 | Prep. 6 |
|---|---|---|---|---|---|---|
| Culture medium | MRS® | MRS® | MRS® | MRS® | MRS® | MRS® + Trealose 1% |
| pH | n.c. | n.c. | n.c. | 5.5 | 5.5 | 5.5 |
| P-CO2 (bar) | 0.8 bar-30 min. | 0.8 bar-30 min. | 1 bar-60 min. | 1 bar-60 min. | n.c. | 0.8 bar-45 min. |
| Stirring speed (rpm) | 100 | 150 | 150 | 150 | 150 | 150 |
| Biomass weight (g) | 40 | 40 | 32 | 35 | 47 | 62 |
| OD 625 nm-T0 | 3.50 | 0.075 | 0.041 | 0.045 | 0.036 | 0.04 |
| OD 625 nm-8 ore | 0.087 | 1.78 | 1.406 | 1.63 | 1.553 | 1.50 |
| CFU/ml-T0 | 3.50E+06 | 2.50E+07 | 6.30E+07 | 3.30E+07 | 3.00E+07 | 1.75E+07 |
| CFU/ml-8 ore | 2.30E+09 | 1.10E+09 | 1.90E+09 | 2.20E+09 | 2.60E+09 | 1.05E+09 | n.c.: non controlled

The CFU number of *Lactobacillus paracasei* LMG S-26420 at the end of the culture was comprised in a range from $1.9 \times 10^9$ to $2.6 \times 10^9$ per millilitre of culture and the biomass produced was comprised from 8 to 16 grams per litre of culture.

The CFU measure was carried out on Petri dish by serial dilution plating of cell mass and microbial colony count.

Cell masses can be maintained at temperatures lower than 0° C. or directly lyophilised to be preserved in solid form or used for pharmaceutical/nutritional preparations.

Example 3

Preparation of the Strain *Lactobacillus paracasei* LMG S-26420 in Lyophilic Form.

The product obtained from the preparation described in Example 2 (Preparation 6) was lyophilised.

To value the effect of a cryoprotectant on the lyophilisation of *Lactobacillus paracasei* LMG S-26420, the lyophilisation processes were carried out in the presence of cyclodextrins, trealose and mannitol.

The cell pellet was suspended in water and an amount of cyclodextrins at 10% (p/V) was added.

The solution was divided in three parts:
Solution A: cyclodextrins 10% (w/V)
Solution B: cyclodextrins 10% (w/V)+trealose 20% (w/V)
Solution C: cyclodextrins 10% (w/V)+mannitol 15% (w/V).

Table 6 reports the lyophilisation process parameters for the solutions A and B.

TABLE 6

| STEPS of lyophilisation process (I) | Parameters |
|---|---|
| Freezing | −50° C., v = 2° C./min, −50° C. × 120 min |
| Primary drying | 50° C. × 15 min, −30° C., v = 0.3° C./min, −30° C. × 300 min P = 100 mTorr |
| Secondary drying | 30° C., v = 0.16° C./min, 30° C. × 480 min P = 100 mTorr |
| Total Time | 14 hours |

Table 7 reports the parameter of the lyophilisation process for the solutions C.

TABLE 7

| STEPS of lyophilisation process (I) | Parameters |
|---|---|
| Freezing | −60° C. × 120 min |
| Annealing | −10° C., v = 0.55° C./min −10° C. × 240 min −50° C. × 120 min |
| Primary drying | −18° C., v = 0.16° C./min −18° C. × 600 min P = 120 mTorr |
| Secondary drying | 25° C., v = 0.07° C./min P = 50 mTorr |

The obtained lyophilic strain *Lactobacillus paracasei* LMG S-26420 was stored in bottles or sachets at 4° C.

Example 4

Determination of Glass Transition Temperatures Tg, T'g

The glass transition temperature Tg and T'g of the solutions A and B before lyophilisation was determined by differential scanning calorimeter, using a Diamond DSC instrument, applying cycles of freezing/heating as reported in Table 8.

TABLE 8

| Step | Temperature 1 (° C.) | Temperature 2 (° C.) | Speed (° C./min) |
|---|---|---|---|
| 1 | 25 | −60 | 10 |
| 2 | −60 | 25 | 40 |
| 3 | 25 | 100 | 10 |
| 4 | 100 | −50 | 50 |
| 5 | −50 | 170 | 40 |

The cycle reported in Table 9 was used for the solutions C.

TABLE 9

| Step | Temperature 1 (° C.) | Temperature 2 (° C.) | Speed (° C./min) |
|---|---|---|---|
| 1 | 25 | −60 | 10 |
| 2 | −60 | −10 | 40 |
| 3 | −10 | −10 | Constant for 120 min |
| 4 | −10 | −60 | 40 |
| 5 | −60 | 25 | 40 |

Glass transition temperatures values of solutions Tg and of frozen aqueous solutions, T'g of the solutions A, B and C to be lyophilised are reported in Table 10.

TABLE 10

| Lyophilisation LMG S-26420 | Preparation | T'g (° C.) | Tg (° C.) |
|---|---|---|---|
| Solutions A = cyclodextrins 10% (p/V) | A-1 | −12.25 | 148.55 |
| | A-2 | −12.75 | 140.81 |
| | A-3 | −13.05 | 144.44 |
| B = cyclodextrins 10% (p/V) + Trealose 20% (pN) | B-1 | −26.50 | 112.00 |
| | B-2 | −26.63 | 114.64 |
| | B-3 | −26.54 | 117.54 |
| | B-4 | −26.75 | 112.45 |
| | B-5 | −26.54 | 114.40 |
| | B-6 | −30.58 | 111.93 |
| | B-7 | −34.76 | 116.629 |
| B = cyclodextrins 10% (p/V) + Trealose 20% (p/V) | B-8 | −27.96 | 111.77 |
| | B-9 | −27.50 | 118.40 |
| C = cyclodextrins 10% (p/V) + mannitol 15% | C-1 | $T'g^1$: −36.8 $T'g^2$: −28 $T'g^3$: −14.8 | n.d. |
| | C-2 | −28.4 | 106.00 |

Example 5

Characterization of the Lyophilic Strain *Lactobacillus paracasei* LMG S-26420.

a) Strain Viability Determination

To determine the yield and viability of the strain *Lactobacillus paracasei* LMG S-26420 after the lyophilisation process of the solutions A, B and C prepared according to Example 3, the CFUs of the strain were determined before and after the lyophilisation process, by Petri dish count. The determination was made on an amount of lyophilic product corresponding to 0.5 grams, suspended in 49.5 grams of dilution buffer (MRS®) and diluted as serial dilution until reaching those useful for the count. The diluted product was then deposited on a Petri dish containing 20 mL of MRS® agar medium, previously sterilized in autoclave, and incubated at 37° C. in anaerobiosis for 72 hours.

The determination was carried out on many lyophilic preparations made from the solutions A, B and C and the results are reported in Table 11.

TABLE 11

| Lyophilisation LMG S-26420 | Preparation | Before-lyo UFC/ml ± SD | After-lyo ($T_0$) UFC/g ± SD | Yield percentage (%) lyophilisation process |
|---|---|---|---|---|
| Solution A = | A-1 | $4.6 \pm 0.6 \times 10^{10}$ | $5.6 \pm 0.4 \times 10^{10}$ | $13.9 \pm 0.9$ |
| cyclodextrins | A-2 | $4.0 \pm 0.5 \times 10^{10}$ | $3.4 \pm 0.2 \times 10^{10}$ | $16.6 \pm 1.1$ |
| 10% (w/V) | A-3 | $2.8 \pm 0.5 \times 10^{10}$ | $3.3 \pm 0.5 \times 10^{10}$ | $15.8 \pm 2.9$ |
| B = | B-1 | $3.2 \pm 0.5 \times 10^{10}$ | $2.9 \pm 0.7 \times 10^{10}$ | $26.2 \pm 6.5$ |
| cyclodextrins | B-2 | $4.4 \pm 0.1 \times 10^{10}$ | $3.3 \pm 0.3 \times 10^{10}$ | $22.8 \pm 1.9$ |
| 10% (w/V) + | B-3 | $3.3 \pm 0.1 \times 10^{10}$ | $6.3 \pm 0.3 \times 10^{10}$ | $57 \pm 27.0$ |
| Trealose 20% | B-4 | $2.2 \pm 0.8 \times 10^{10}$ | $3.9 \pm 0.3 \times 10^{10}$ | $45.1 \pm 2.7$ |
| (w/V) | B-5 | $2.8 \pm 0.2 \times 10^{10}$ | $4.6 \pm 0.9 \times 10^{10}$ | $41.7 \pm 7.5$ |
|  | B-6 | $3.6 \pm 0.1 \times 10^{10}$ | $3.7 \pm 0.5 \times 10^{10}$ | $23.3 \pm 2.9$ |
|  | B-7 | $3.1 \pm 0.9 \times 10^{10}$ | $2.9 \pm 0.8 \times 10^{10}$ | $21.9 \pm 6.0$ |
|  | B-8 | $5.5 \pm 0.7 \times 10^{10}$ | $1.4 \pm 0.8 \times 10^{10}$ | $35.8 \pm 1.4$ |
|  | B-9 | $4.3 \pm 0.9 \times 10^{10}$ | $3.7 \pm 0.8 \times 10^{10}$ | $22.6 \pm 2.1$ |
| C = | C-1 | $7.3 \pm 2. \times 10^{10}$ | $<1 \times 10^{10}$ | $13.9 \pm 0.9$ |
| cyclodextrins | C-2 | $3.6 \pm 0.5 \times 10^{10}$ | $2.3 \pm 0.8 \times 10^{10}$ | $9.56 \pm 4.0$ |
| 10% (p/V) + |  |  |  |  |
| mannitol 15% |  |  |  |  |

Table 11 confirms the effect of trealose during the lyophilisation process, leading to a recovery higher than 30% in CFU.

Mannitol can be added to trealose if a bigger lyophilic mass is desired, in particular for small dosages of *Lactobacillus paracasei* LMG S-26420.

Example 6

Determination of Water Activity and Weight Loss by Drying Lyophilic *Lactobacillus paracasei* LMG S-26420.

a) Determination of the Water Activity ($a_w$)

The determination of the water activity corresponds to the determination of free water in lyophilic preparations of *Lactobacillus paracasei* LMG S-26420 of the solutions A, B and C prepared following Example 3. The determination was carried out by placing a sample of about 1 gram of each lyophilic product in an Aqualab VSA Decagon instrument that measures water activity of a sample with a humidity dielectric detector, directly giving the measure that is directly proportional to the water moles over the sample moles and the obtained values are reported in Table 12.

TABLE 12

| Lyophilisation components LMG S-26420 | Preparation No. | $a_w$ (water activity) |
|---|---|---|
| Solution A = cyclodextrins | A-1 | n.d |
| 10% (w/V) | A-2 | n.d. |
|  | A-3 | 0.358 |
| B = cyclodextrins 10% | B-1 | n.d |
| (w/V) + | B-2 | n.d |
| Trealose 20% (w/V) | B-3 | 0.363 |
|  | B-4 | 0.153 |
|  | B-5 | 0.100 |
| B = cyclodextrins 10% | B-6 | 0.120 |
| (w/V) + | B-7 | 0.136 |
| Trealose 20% (w/V) | B-8 | 0.166 |
|  | B-9 | 0.087 |
| Solution C = cyclodextrins | C-1 | 0.174 |
| 10% (w/V) + mannitol 15% | C-2 | 0.134 |
| (w/V) |  |  |

All obtained lyophilic have $a_w$ values lower than 0.6 confirming that they can be stored for long periods without risks of degradation.

b) Determination of the Loss of Water Content (LOD)

The humidity content of the lyophilic samples was obtained using a thermoscales Mettler and values are reported in Table 13.

TABLE 13

| Lyophilisation components LMG S-26420 | Preparation No. | Humidity Percentage LOD (%) |
|---|---|---|
| Solution A = | A-1 | 3.61 |
| cyclodextrins 10% (w/V) | A-2 | 2.58 |
|  | A-3 | 3.9 |
| B = cyclodextrins 10% (w/V) + | B-1 | 4.01 |
| Trealose 20% (w/V) | B-2 | 4.24 |
| B = cyclodextrins 10% (w/V) + | B-3 | 4.90 |
| Trealose 20% (w/V) | B-4 | 3.39 |
|  | B-5 | 2.94 |
|  | B-6 | 2.85 |
|  | B-7 | 3.05 |
|  | B-8 | 3.21 |
|  | B-9 | 2.41 |
| Solution C = | C-1 | 2.14 |
| cyclodextrins 10% (w/V) + |  |  |
| mannitol 15% (w/V) |  |  |

Example 7

Determination of Stability of Lyophilic Preparations of the Strain *Lactobacillus paracasei* LMG S-26420.

The lyophilic preparations of the strain *Lactobacillus paracasei* LMG S-26420 were placed at 4° C. and their stability was determined by measuring the bacterial charge and the water activity ($a_w$) (T0), at time zero, 3 and 6 months. The obtained results are reported in Table 14.

TABLE 14

| Prepa- ration | CFU/g ± SD | | | Yield CFU % | $a_w$ (water activity) | $a_w$ (water activity) |
|---|---|---|---|---|---|---|
|  | T0 | T3 | T6 | T6/T0 | T0 | T6 |
| A-1 | $3.4 \pm 0.2 \times 10^{10}$ | $1.3 \pm 0.2 \times 10^{10}$ | $9.8 \pm 5.7 \times 10^{4}$ | <10% |  |  |

TABLE 14-continued

| Prepa-ration | CFU/g ± SD T0 | CFU/g ± SD T3 | CFU/g ± SD T6 | Yield CFU % T6/T0 | $a_w$ (water activity) T0 | $a_w$ (water activity) T6 |
|---|---|---|---|---|---|---|
| A-2 | 3.5 ± 0.6 × $10^{10}$ | 6.4 ± 1.5 × $10^9$ | <1.78 × $10^2$ | <10% | | |
| A-3 | 2.9 ± 0.7 × $10^{10}$ | 7.1 ± 2.5 × $10^9$ | — | | | |
| B-1 | 2.9 ± 0.7 × $10^{10}$ | 7.1 ± 2.5 × $10^9$ | — | | | |
| B-2 | 3.3 ± 0.3 × $10^{10}$ | 1.2 ± 0.1 × $10^{10}$ | — | | 0.153 | 0.276 |
| B-3 | 6.3 ± 0.2 × $10^{10}$ | 1.9 ± 0.2 × $10^{10}$ | 1.8 ± 0.1 × $10^{10}$ | 27.7 ± 1.0 | 0.100 | 0.163 |
| B-4 | 3.9 ± 0.2 × $10^{10}$ | 2.3 ± 0.6 × $10^{10}$ | 2.9 ± 0.7 × $10^{10}$ | 75.0 ± 19.2 | 0.120 | 0.313 |
| B-5 | 4.6 ± 0.9 × $10^{10}$ | 4.9 ± 0.4 × $10^{10}$ | — | | 0.136 | 0.279 |
| B-6 | 3.7 ± 0.5 × $10^{10}$ | 4.2 ± 0.3 × $10^{10}$ | 5.0 ± 0.6 × $10^{10}$ | 136.2 ± 14.8 | 0.143 | 0.182 |
| B-7 | 2.9 ± 0.8 × $10^{10}$ | 1.9 ± 0.3 × $10^{10}$ | 2.6 ± 2.1 × $10^{10}$ | 91.1 ± 17.9 | 0.087 | — |

The table shows that the lyophilic products obtained in the presence of trealose are stable at 4° C. for 6 months and that the water activity ($a_w$) is always lower than 0.6.

Example 8

Compositions Comprising *Lactobacillus paracasei* LMG S-26420 in Sachets

The preparations in sachets comprise an amount of lyophilic product, prepared as in Example 2 (preparations B), of 800 mg and 500 mg, corresponding respectively to about $3 \times 10^{10}$ and $2 \times 10^{10}$ living cells of *Lactobacillus paracasei* LMG S-26420.

The lyophilic product was mixed with excipients, preventively sieved, and the homogeneous mixture was divided in sachets. The unitary compositions are reported in Table 15.

Among the described compositions, one comprises inuline, another comprises xilo-oligosaccharide and the others a mixture of fructo-oligosaccharides formed by a chain of fructose molecules bound to a molecule of glucose (ACTILIGHT® 950P).

TABLE 15

| Component | Comp. 1 weight (mg) | Comp. 2 weight (mg) | Comp. 3 weight (mg) | Comp. 4 weight (mg) |
|---|---|---|---|---|
| *Lactobacillus paracasei* lyophilic LMG S-26420 | 800 | 800 | 500 | 500 |
| Inulin | 3200 | | | |
| Xilo-oligosaccharide | | 3200 | 506 | 506 |
| Flavour (Passion fruit) | | | 44 | 44 |
| Silica | | | 10 | 10 |
| Astaxantine | | | | 160 |
| ACTILIGHT® 950P | | | 2940 | 1720 |
| Total weight | 4000 | 4000 | 4000 | 4000 |

The compositions can comprise vitamins, like for example vitamin E, vitamin B1, vitamin B2, vitamin B16.

The compositions in sachets can be suspended in water solutions or in semi-solid foods.

Example 9

Compositions Comprising *Lactobacillus paracasei* LMG S-26420 in Tablets

The preparations in tablets containing an amount of 250 mg of lyophilic product, corresponding to about $1 \times 10^{10}$ living cells of *Lactobacillus paracasei* LMG S-26420, were obtained by mixing a lyophilic with excipients preventively sieved on a net of 800 micron. The mixture was then compressed in a Ronchi compressing machine or an analogous machine by applying a compressing force of about 13 KN.

The unitary composition of the tablets is reported in Table 16.

TABLE 16

| Components | Amount (mg) |
|---|---|
| *Lactobacillus paracasei* LMG S-26420 | 250 (1 × $10^{10}$ CFU) |
| Isomalto | 278.0 |
| Croscarmellose | 9.9 |
| Talc | 5.5 |
| Silica | 3.8 |
| Magnesium stearate | 2.8 |
| Total weight | 550 |

The invention claimed is:

1. A process of producing a lyophilized preparation of *Lactobacillus paracasei* LMG S-26420 strain deposited at Belgian Coordinated Collection of Microorganism,
BCCM/LMG Bacteria Collection,
Universiteit Gent,
Laboratorium voorMicrobiologies,
K.L. Ledeganckstraat, 35
9000 Gent,
with the accession number LMG S-26420, wherein the deposited *Lactobacillus paracasei* LMG S-26420 strain is capable of converting linoleic acid to conjugated linoleic acid in a percentage higher than 30%, said method comprising the steps of:
inoculating the *Lactobacillus paracasei* LMG S-26420 strain in to a suitable culture broth, separating the bacterial mass of the strain from the culture broth by centrifugation and lyophilizing the centrifuged *Lactobacillus paracasei* LMG S-26420 strain.

2. The process of claim 1, wherein the step of lyophilizing is carried out in the presence of cryoprotectants selected among soluble carbohydrates.

3. The process of claim 2, wherein the lyophilizing step is carried out in the presence of trealose.

4. The process of claim 1, wherein higher than $10^9$ colony forming units per milliliter of the culture broth and higher than 4 grams of the biomass per liter of the culture broth of the *Lactobacillus paracasei* LMG S-26420 strain are obtained.

5. The process of claim 1, wherein the inoculating step is carried out in a volumetric percentage from 0.1% to 10% at a temperature of 30° C. to 37° C. at a pH of 4.5 to 7.5 for a period of 6 to 15 hours.

6. The process of claim 1, wherein the *Lactobacillus paracasei* LMG S-26420 strain has the capacity to convert the linoleic acid to isomers of conjugated linoleic acid c9-c11 and t9-t11 with biological activity, wherein the sum thereof is in a percentage higher than 30% compared to other conjugated linoleic acid isomers.

7. A process of producing a nutritional composition, pharmaceutical composition or food comprising:
mixing the lyophilized preparation of the deposited *Lactobacillus paracasei* LMG S-26420 strain obtained by the process of claim 1 with acceptable excipients in the form of tablets, capsules, liquid suspension, or granules for sachet.

8. The process of claim 7, wherein the *Lactobacillus paracasei* LMG S-26420 strain is present in an amount ranging from $1\times10^8$ to $5\times10^{11}$.

9. The process of claim 7, wherein the nutritional composition, the pharmaceutical composition or the food comprises prebiotics, vitamins, and mineral salts.

10. The process of claim 9, wherein the prebiotics are selected from the group consisting of fructo-oligosaccharides, inulines, galacto-oligosaccharides, xylo-oligosaccharides, and isomalto-oligosaccharides, and the vitamins are selected from the group consisting of vitamin E and vitamin B.

11. The process of claim 7, wherein the nutritional composition, the pharmaceutical composition or the food further comprises *Bifidobacteria*.

* * * * *